(12) United States Patent
Qi et al.

(10) Patent No.: US 10,570,132 B2
(45) Date of Patent: Feb. 25, 2020

(54) PROCESS FOR PREPARING AN INTERMEDIATE FOR AVIBACTAM

(71) Applicant: XINFA PHARMACEUTICAL CO., LTD, Dongying (CN)

(72) Inventors: Yuxin Qi, Dongying (CN); Xinfa Li, Dongying (CN); Baolin Wang, Dongying (CN); Hu Qu, Dongying (CN); Xin Xu, Dongying (CN); Lizhu Ju, Dongying (CN)

(73) Assignee: XINFA PHARMACEUTICAL CO., LTD, Dongying (CN)

( * ) Notice: Subject to any disclaimer, the term of this patent is extended or adjusted under 35 U.S.C. 154(b) by 0 days.

(21) Appl. No.: 16/345,749

(22) PCT Filed: Mar. 6, 2018

(86) PCT No.: PCT/CN2018/078070
§ 371 (c)(1),
(2) Date: Apr. 29, 2019

(87) PCT Pub. No.: WO2019/075984
PCT Pub. Date: Apr. 25, 2019

(65) Prior Publication Data
US 2019/0263812 A1 Aug. 29, 2019

(30) Foreign Application Priority Data
Oct. 18, 2017 (CN) .......................... 2017 1 0968060

(51) Int. Cl.
*C07D 471/08* (2006.01)
*C07D 211/60* (2006.01)
*C07B 57/00* (2006.01)

(52) U.S. Cl.
CPC ............ *C07D 471/08* (2013.01); *C07B 57/00* (2013.01); *C07D 211/60* (2013.01)

(58) Field of Classification Search
None
See application file for complete search history.

(56) References Cited

FOREIGN PATENT DOCUMENTS

WO    WO-2014135930 A1 * 9/2014 ........... C07D 471/08

* cited by examiner

*Primary Examiner* — Zinna Northington Davis
(74) *Attorney, Agent, or Firm* — CBM Patent Consulting, LLC

(57) ABSTRACT

A method for preparing an intermediate for avibactam, and specifically relates to a method for preparing ({[(2S,5R)-2-carbamoyl-7-oxo-1,6-diazabicyclo[3.2.1]oct-6-yl]oxy}sulfonyl)tetrabutylammonium salt (II). With 5R-[(benzyloxy) amino] piperidine-2S-carboxylate oxalate (III) as the raw material is reacted with the amide of Formula IV via amidation to prepare the compound of Formula V; the resulting compound of Formula V is reacted with the carbonylation reagent via urea cyclization to obtain the compound of Formula VI; the benzyl or the substituted benzyl in the compound of Formula VI is removed by catalytic hydrogenation, then the resulting compound is sulfatated by sulfur trioxide complex and is salinized into tetrabutylammonium to obtain the final product (II).

19 Claims, No Drawings

PROCESS FOR PREPARING AN INTERMEDIATE FOR AVIBACTAM

FIELD

The present application relates to the field of pharmaceutical biochemical engineering, specifically relates to a process for preparing an intermediate for avibactam, and more specifically relates to a simple process for preparing ({[(2S, 5R)-2-carbamoyl-7-oxo-1,6-diazabicyclo[3.2.1]oct-6-yl]oxy} sulfonyl)tetrabutylammonium salt.

BACKGROUND

Avibactam, which is one of diazabicyclooctanone compounds, as a non-β-lactam inhibitor, may inhibit type A (including ESBL and KPC) and type C of β-lactamases. When co-administered with various types of cephalosporins and carbapenem antibiotics, avibactam has a broad-spectrum activity against bacteria, particularly has a significant activity against *Escherichia coli* and *Klebsiella pneumoniae* containing extended-spectrum β-lactamases, *Escherichia coli* containing surplus AmpC enzyme, and *Escherichia coli* containing both AmpC and extended-spectrum β-lactamases. Avibactam (I), [(1R,2S,5R)-2-(aminocarbonyl)-7-oxo-1,6-diazabicyclo[3.2.1]oct-6-yl] sodium sulphate with CAS No. 1192491-61-4, has a structural formula represented by Formula I:

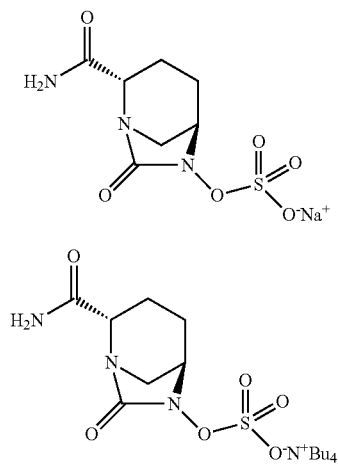

Patent literatures CN103649051A, CN105294690A, CN106866668A, WO2012086241, U.S. Pat. Nos. 8,148,540, 9,284,273, and 9,567,335 disclosed preparation of (2S,5R)-6-benzyloxy-7-oxo-1,6-diazabicyclo [3.2.1] octane-2-formamide by use of 5R-[(benzyloxy) amino] piperidine-2S-carboxylate oxalate (III) as the raw material via a route of amidation followed by urea cyclization or a route of urea cyclization followed by amidation, and then the prepared (2S,5R)-6-benzyloxy-7-oxo-1,6-diazabicyclo [3.2.1] octane-2-formamide was subjected to debenzylation by palladium-on-carbon catalytic hydrogenolysis, followed by sulphation by sulfur trioxide complex, ammonium salinization, and ion exchange, thereby producing avibactam (I), referring to Scheme 1.

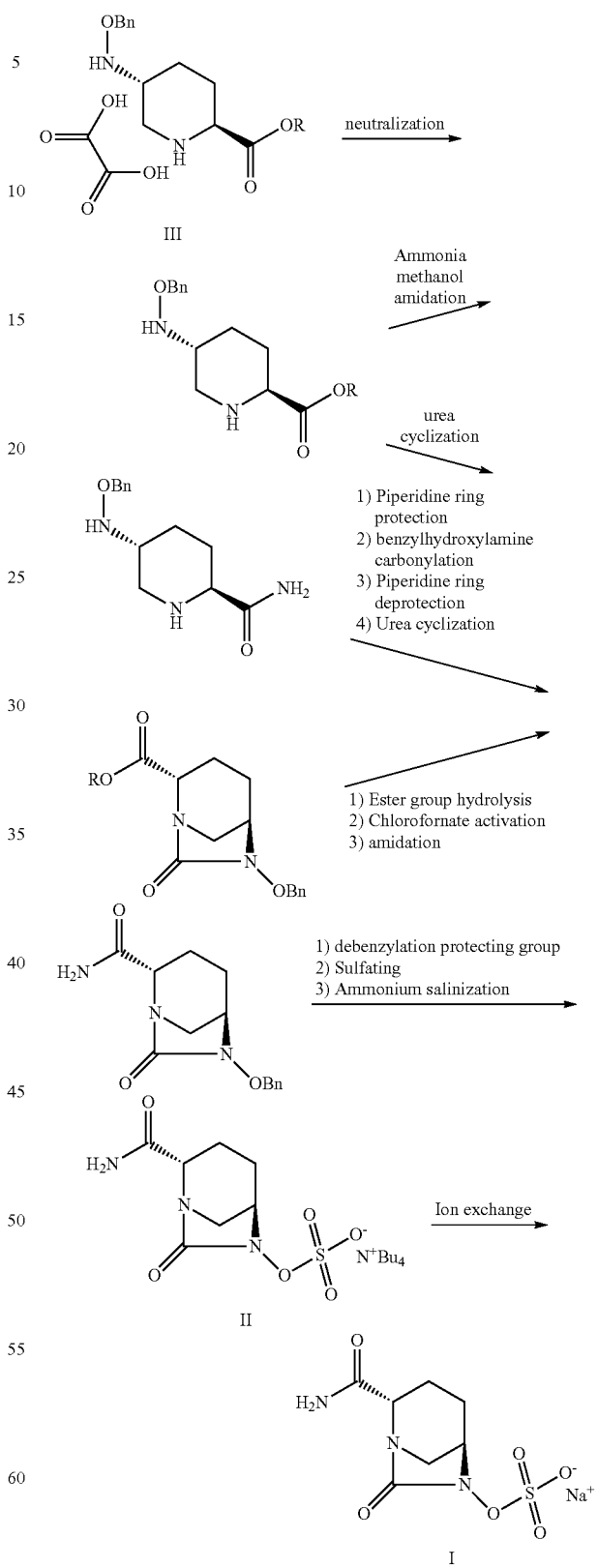

1. In the process of amidation followed by urea cyclization, firstly 5R-[(benzyloxy) amino] piperidine-2S-carboxylate oxalate (III) is amidated by an ammonia-methanol solution or an ammonium hydroxide-alcohol solution to obtain (2S,5R)-5-[(benzyloxy)amino]piperidine-2-formamide; then (2S,5R)-6-benzyloxy-7-oxo-1,6-diazabicyclo [3.2.1]octane-2-formamide (with a total yield of 61.2%~89.1%) is obtained through steps of protection of the amino of piperidine ring by 9-fluorenylmethyl chloroformate (FMOC-CL) or di-tert-butyl dicarbonate, reacting carbonyl diimidazole with benzyloxylamine via carbonylation, deprotection of the piperidine ring by diethylamine, and then urea cyclization.

In this process, amide group is present after amidation, such that it is demanding on urea cyclization reaction, where inexpensive and readily accessible triphosgene or diphosgene cannot be used. This is because under the action of triphogene or diphosgene, amide groups are easily dehydrated to produce cyanide; with a high content of byproducts and difficulty to purify, referring to Scheme 2.

Scheme 2

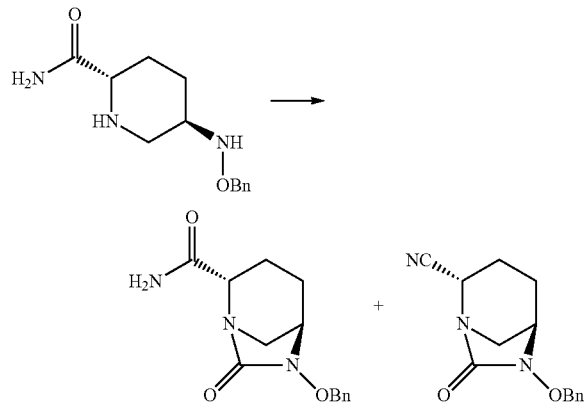

Even if carbonyl diimidazole (CDI) with a high selectivity is used as the urea cyclization reagent, the 9-fluorenylmethyl chloroformate (FMOC-CL) or di-tert-butyl dicarbonate is still needed to protect the aminos of piperidine ring; otherwise, because carbonyl diimidazole and the two aminos (amino of piperidine ring and benzyloxylamino) have similar reaction activities, producing derivatives where imidazole carbonyl is introduced on the two nitrogen atoms with the molar ratio of the two derivatives being about 1:1, while the imidazole carbonyl of the piperidine ring preferably reacts with the ortho-position carboxamide group, the target product cannot be obtained, and the product yield is lower than 50%, referring to Scheme 3:

Scheme 3

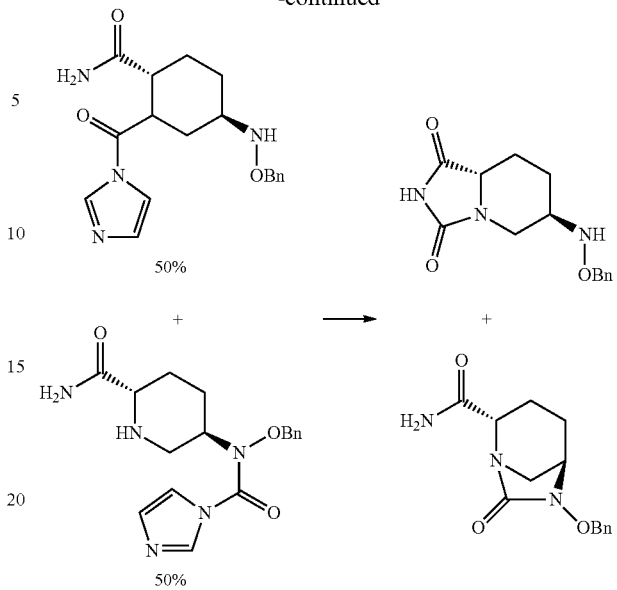

9-fluorenylmethyl chloroformate (FMOC-CL) or di-tert-butyl dicarbonate protecting agent has a high price; besides, they only provide one carbonyl group; therefore, the reaction atomic economy is poor and the operation process is tedious.

2. In the process of urea cyclization followed by amidation, (2S,5R)-6-benzyloxy-7-oxo-1,6-diazabicyclo[3.2.1] octane-2-carboxy acid is obtained through steps of urea cyclization of 5R-[(benzyloxy) amino] piperidine-2S-carboxylate oxalate (III) by a urea cyclization reagent (triphosgene-organic base, carbonyl diimidazole or other carbonylation agent) followed by hydrolysis in an alkaline condition such as lithium hydroxide aqueous solution; and then (2S,5R)-6-benzyloxy-7-oxo-1,6-diazabicyclo[3.2.1]octane-2-formamide is obtained through steps of activating carboxyl into anhydrides by trimethylacetyl chloride or other reagent, followed by amidation by the ammonium hydroxide, with a total yield of 34.5-65.5%. Benzyl (2S, 5R)-6-benzyloxy-7-oxo-1,6-diazabicyclo [3.2.1] octane-2-carboxylate obtained after urea cyclization has a low activity, which cannot be amidated in an ammonia-methanol solution; instead, an effective amidation can only be realized by first hydrolysis of the ester group into carboxyl and then activating the carboxyl into anhydrides; therefore, more operation steps are involved.

Therefore, neither of the processes above facilitates simple industrial production of the intermediate for avibactam, namely, ({[(2S,5R)-2-carbamoyl-7-oxo-1,6-diazabicyclo[3.2.1]oct-6-yl]oxy}sulfonyl)tetrabutylammonium salt (II).

SUMMARY

To address the drawbacks in the prior art, the present application provides a simple process for preparing an intermediate for avibactam, namely, ({[(2S,5R)-2-carbamoyl-7-oxo-1,6-diazabicyclo[3.2.1]oct-6-yl]oxy} sulfonyl) tetrabutylammonium salt (II), which has an easily operable reaction condition, a strong operability, a streamlined process, a low cost, less byproducts, a high atomic economy for the reaction, and a high purity and a high yield for product (II). Avibactam (I) may be obtained through ion exchange of the prepared product (II).

Definition of Terms

Compound of Formula II: intermediate for avibactam, namely, ({[(2S,5R)-2-carbamoyl-7-oxo-1,6-diazabicyclo[3.2.1]oct-6-yl]oxy}sulfonyl)tetrabutylammonium salt, where -Bu$_4$ in the structural formula refers to tetrabutyl;

Compound of Formula III: 5R-[(benzyloxy) amino] piperidine-2S-carboxylate oxalate, where -Bn refers to benzyl;

Compound of Formula V: N,N-di(substituted)benzyl-5R-benzyloxyamino piperidine-2S-formamide, where -Bn refers to benzyl;

Compound of Formula VI: N,N-di(substituted)benzyl-(2S,5R)-6-benzyloxy-7-oxo-1,6-diazabicyclo[3.2.1]oct-2-formamide; where -Bn refers to benzyl.

The numbering of the compounds in the specification is completely consistent with the numbering of their structural formulae, and they have same references.

A technical solution of the present application is provided below:

A process for preparing an intermediate for avibactam, comprising the following steps:

1) a compound of Formula III is reacted with an amide of Formula IV in solvent A and in the presence of base A via an amidation reaction to obtain a compound of Formula V;

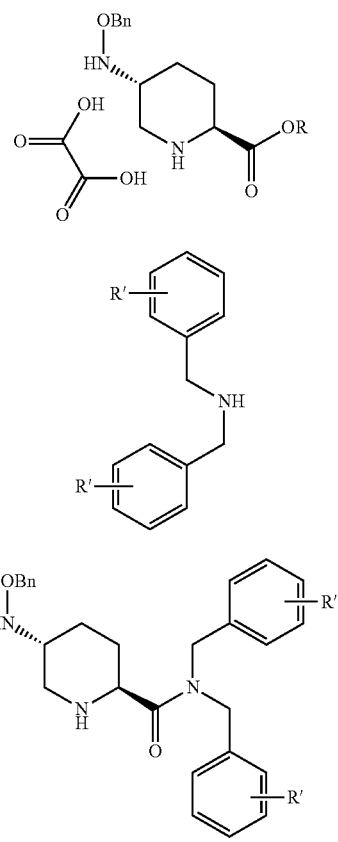

where in the compound of Formula III: R refers to a C$_{1-6}$ aliphatic group or C$_{1-6}$ alkyl-substituted phenyl; preferably, R is selected from the group consisting of methyl, ethyl, n-propyl, isopropyl, n-butyl, isobutyl, tert-butyl, n-pentyl, isopentyl, tert-amyl, hexyl, benzyl, o-methylbenzyl and p-methylbenzyl;

in the compound of Formula IV: R' is selected from the group consisting of hydrogen, o-methoxy, o-methyl, p-methoxy and p-methyl;

R' in the compound of formula V is identical to R' in the compound of formula IV; 2) the compound of formula V is reacted with a carbonylation reagent in solvent B and in the presence of base B via urea cyclization to obtain the compound of Formula VI;

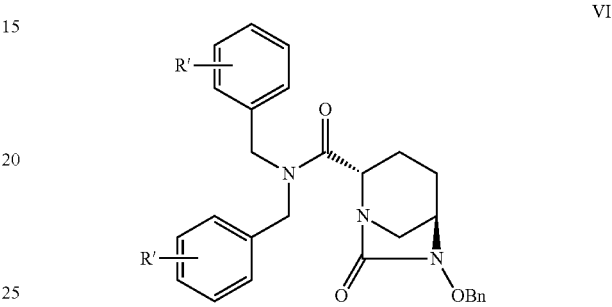

where R' in the compound of formula VI is identical to R' in the compound of formula IV;

3) in solvent C and in the presence of base C, the benzyl or the substituted benzyl in the compound of Formula VI is removed by catalytic hydrogeneration, then the resulting compound is sulfatated by sulfur trioxide complex, to obtain a product; then, the product is salinized into tetrabutylammonium to obtain the compound of Formula II:

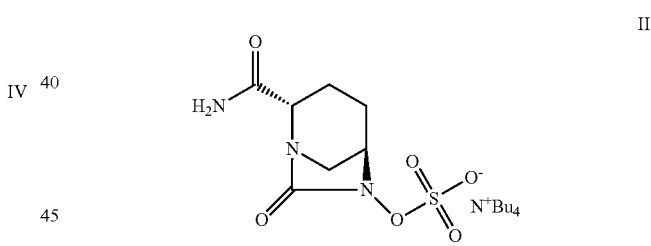

Preferably according to the present application, solvent A in step (1) is selected from the group consisting of dichloromethane, 1,2-dichloroethane, trichloromethane, tetrachloromethane, tetrahydrofuran, 2-methyltetrahydrofuran, methoxycyclopentane, methylbenzene, and combinations of two or more thereof.

Preferably according to the present application, in step (1), a mass ratio between solvent A and the compound of Formula III is 4~20:1.

Preferably according to the present application, in step (1), base A is an inorganic base or an organic base; preferably, the inorganic base is one of potassium carbonate or sodium carbonate, or a mixture of the two, and the organic base is dibenzylamine.

Preferably according to the present application, in step (1), a molar ratio between base A and the compound of Formula III is 2.0~5.0:1.

Preferably according to the present application, in step (1), the amide of Formula IV is selected from the group consisting of dibenzylamine, di(o-methoxy) benzylamine, di(p-methoxy) benzylamine, di(o-methyl) benzylamine, and di(p-methyl) benzylamine.

Preferably according to the present application, in step (1), a molar ratio between the amide of Formula IV and the compound of Formula III is 1~4:1.

Preferably according to the present application, in step (1), the amidation reaction is conducted in the temperature of from 0° C. to 100° C.; preferably, the amidation reaction is conducted in the temperature of from 30° C. to 80° C. The reaction duration ranges from 1 to 8 hours.

Preferably according to the present application, in step (2), solvent B is selected from the group consisting of dichloromethane, 1,2-dichloroethane, trichloromethane, tetrachloromethane, tetrahydrofuran, 2-methyltetrahydrofuran, methoxycyclopentane, n-butanol, tert-butanol or methylbenzene, and combinations of two or more thereof.

Preferably according to the present application, in step (2), a mass ratio between solvent B and the compound of formula V is 4~27:1.

Preferably according to the present application, in step (2), base B is an organic base; preferably, the organic base is triethylamine or tri-n-butylamine.

Preferably according to the present application, in step (2), a molar ratio between base B and the compound of formula V is 2~6:1.

Preferably according to the present application, in step (2), a molar ratio between the carbonylation reagent and the compound of Formula V is 0.3~3:1.

Preferably according to the present application, in step (2), the carbonylation reagent is selected from the group consisting of triphosgene, diphosgene, carbonyldiimidazole and di-tert-butyl dicarbonate.

Preferably, a molar ratio between triphosgene and the compound of formula V is 0.3~1.5:1; a molar ratio between diphosgene and the compound of formula V is 0.5~2.0:1; a molar ratio between carbonyldiimidazole or di-tert-butyl dicarbonate and the compound of formula V is 1.0~3.0:1.

Preferably according to the present application, in step (2), the temperature for the urea cyclization reaction ranges from −20° C. to 100° C.; preferably, the urea cyclization reaction temperature ranges from 10 to 40° C. The reaction duration ranges from 4 hours to 10 hours.

Preferably according to the present application, in step (3), solvent C is selected from the group consisting of isopropanol, n-butanol, tert-butanol, tetrahydrofuran, N,N-dimethyl formamide, water, and mixtures of two or more thereof.

Preferably according to the present application, in step (3), a mass ratio between solvent C and the compound of Formula VI is 4~20:1.

Preferably according to the present application, in step (3), base C is organic base; preferably, the organic base is triethylamine.

Preferably according to the present application, in step (3), a molar ratio between base C and the compound of Formula VI is 0.1~0.3:1.

Preferably according to the present application, in step (3), the catalyst for the catalytic hydrogenolysis is palladium-on-carbon with 5% mass content of palladium or palladium-on-carbon with 10% mass content of palladium; in the palladium-on-carbon, the water content is 5~55 wt %.

Preferably according to the present application, in step (3), the mass of the catalyst for the catalytic hydrogenolysis is 1.0~20.0% of the mass of the compound of formula VI; the hydrogen pressure used in the catalytic hydrogenolysis is 0.05~0.30 Mpa.

Preferably according to the present application, in step (3), the sulfur trioxide complex is one of trimethylamine sulfur trioxide, pyridine sulfur trioxide, or triethylamine sulfur trioxide.

Preferably according to the present application, a molar ratio between the sulfur trioxide complex and the compound of formula VI is 1.0~2.0:1.

Preferably according to the present application, in step (3), a tetrabutyl ammonium source used for the tetrabutylammonium salinization is tetrabutylammonium hydroxide or tetrabutylammonium acetate.

Preferably according to the present application, in step (3), a molar ratio between the tetrabutyl ammonium source used for the tetrabutylammonium salinization and the compound of formula VI is 0.8~1.2:1.

Preferably according to the present application, in step (3) the reaction temperatures for the catalytic hydrogenolysis and the sulfatation both range from −10° C. to 60° C.; further preferably, the reaction temperatures for the catalytic hydrogenolysis and the sulfatation both range from 10° C. to 40° C. The catalytic hydrogenolysis and the sulfatation are "one-pot process" reactions.

Preferably according to the present application, in step (3), the reaction durations for the catalytic hydrogenolysis and the sulfatation are both 1~6 hours.

Preferably according to the present application, in step (3), the reaction temperature for the tetrabutylammonium salinization ranges from 0° C. to 50° C.; preferably, the reaction temperature for the tetrabutylammonium salinization ranges from 10° C. to 30° C.

Preferably according to the present application, in step (3), the reaction duration for the tetrabutylammonium salinization is 1~15 hours; preferably, the reaction duration for the tetrabutylammonium salinization is 2~4 hours.

In the present application, N,N-di(substituted)benzyl-5R-benzyloxyamino piperidine-2S-formamide (V) is obtained through a step of amidating 5R-[(benzyloxy) amino] piperidine-2S-carboxylate oxalate (III) as the raw material with the amide of Formula IV; the resulting compound V is urea cyclized by carbonylation reagent to obtain N,N-di(substituted)benzyl-(2S,5R)-6-benzyloxy-7-oxo-1,6-diazabicyclo[3.2.1]oct-2-formamide (VI); through steps of removing the benzyl or the substituted benzyl in the compound VI by catalytic hydrogenolysis, followed by sulfatation by sulfur trioxide complex, and tetrabutylammonium salinization, ({[(2S,5R)-2-carbamoyl-7-oxo-1,6-diazabicyclo[3.2.1]oct-6-yl]oxy}sulfonyl)tetrabutylammonium salt (II) is prepared (Scheme 4); by ion exchange of the resulting compound of formula II, the avibactam (I) may be prepared.

Scheme 4

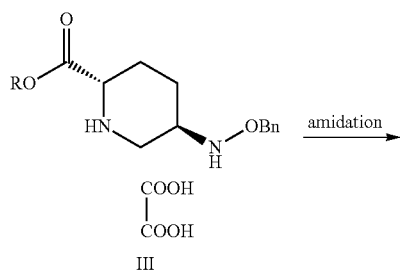

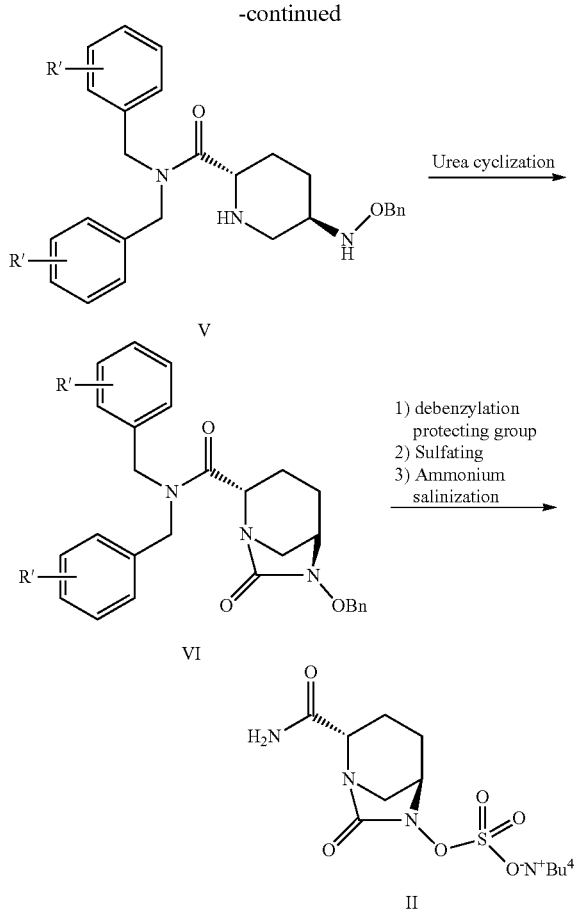

(The present application provides the following beneficial effects:
1. The obtained N,N-di(substituted)benzyl-5R-benzyloxyaminopiperidine-2S-formamide (V) obtained according to the present application has a high stability, and the process of the present application avoids the side reaction at its 2-position carboxamide from the perspective of designed reaction; besides, it does not require protecting the piperidine ring, and a carbonylation reagent which is inexpensive and easily accessible may be directly used for urea cyclization; the reaction condition is easily operable; the preparing process has a strong operability, a simple process, a high reaction atomic economy, and a low cost.
2. Further and also unexpectedly, N,N-di(substituted)benzyl-(2S,5R)-6-benzyloxy-7-oxo-1,6-diazabicyclo[3.2.1]oct-2-formamide (VI) has an appropriate hydrogenolysis activity, which reduces accumulation of the hydrogenolysis product (2S,5R)-6-hydroxyl-7-oxo-1,6-diazabicyclo[3.2.1]oct-2-formamide in the system; once the hydrogenolysis product is generated, sulphating may be carried out in time; besides, the resulting product (II) has a high purity and yield.

EXAMPLES

Hereinafter, the present application will be illustrated in detail with reference to the examples; however, the present application is not limited thereto.

The percentages in the examples all refer to mass percentages, unless otherwise indicated.

The raw material 5R-[(benzyloxy) amino] piperidine-2S-carboxylate oxalate (III) is easily accessible in the market (from Jinan Qinsi Pharmaceutical Company), which is a white powder with an optical purity of 99.6%.

The reaction process and product purity were monitored by liquid chromatograph. A liquid chromatograph equipped with a chiral column (ES-OVS, 150 mm×4.6 mm, Agilent) is used to detect the optical purity (area ratio %) and calculate the yield and e.e % value.

Example 1: Preparation of N, N-dibenzyl-5R-[(benzyloxy)amino]piperidine-2S-formamide ($V_1$)

To a 500 ml 4-neck flask equipped with a stirrer and a thermometer were charged 250 g of tetrahydrofuran, 28.0 g of potassium carbonate, 43.0 g (0.1 mol) of benzyl 5R-[(benzyloxy)amino]piperidine-2S-carboxylate oxalate (III), and 30 g (0.15 mol) of dibenzylamine, and then the reaction mixture was stirred for 5 hours between 40° C. to 45° C., then cooled to 20° C.~25° C., and filtered. The filter cake was washed twice with tetrahydrofuran, 30 g for each time. Organic phases were combined and distilled to recover tetrahydrofuran. 40 g of methyl tert-butyl ether was charged to the residue, then mashed and washed, and filtered to obtain 41.1 g of N, N-dibenzyl-5R-[(benzyloxy)amino]piperidine-2S-formamide in a yield of 95.8% and a purity of 99.92% in HPLC.

NMR (Nuclear Magnetic Resonance) data of the resulting product are provided below: $^1$H-NMR (400 MHz, DMSO-$d_6$)

$^1$H-NMR (400 MHz, DMSO-d6) δ: 1.12 (1H, q), 1.29 (1H, q), 1.86 (2H, d), 2.29 (1H, t), 2.76 (1H, m), 2.95 (1H, d), 3.18 (1H, d), 4.62 (4H, s), 4.83 (2H, s), 6.50 (1H, d), 7.28-7.47 (15H, m).

Example 2: Preparation of N, N-dibenzyl-5R-[(benzyloxy)amino]piperidine-2S-formamide ($V_1$)

To a 500 ml 4-neck flask equipped with a stirrer and a thermometer were charged 300 g of 1,2-dichloroethane, 43.0 g (0.1 mol) of benzyl 5R-[(benzyloxy)amino]piperidine-2S-carboxylate oxalate (III), and 60 g (0.30 mol) of dibenzylamine, and then the reaction mixture was stirred for 4 hours between 50° C. to 55° C., then cooled to 20° C.~25° C., and filtered. The filter cake was washed twice with 1,2-dichloroethane, 30 g for each time. Organic phases were combined and distilled to recover 1,2-dichloroethane. 50 g of methyl tert-butyl ether was charged to the residue, then mashed and washed, and filtered to obtain 40.5 g of N, N-dibenzyl-5R-[(benzyloxy) amino] piperidine-2S-formamide in a yield of 94.4% and a purity of 99.86% in HPLC.

Example 3: Preparation of N,N-di(p-methoxybenzyl)-5R-[(benzyloxy)amino]piperidine-2S-formamide ($V_2$)

To a 500 ml 4-neck flask equipped with a stirrer and a thermometer were charged 250 g of tetrahydrofuran, 28.0 g of potassium carbonate, 37.0 g (0.1 mol) of ethyl 5R-[(benzyloxy)amino]piperidine-2S-carboxylate oxalate (III), and 40 g (0.16 mol) of di(p-methoxy)benzylamine, and then the reaction mixture was stirred for 4 hours between 50° C. to 55° C., then cooled to 20° C.~25° C., and filtered. The filter cake was washed twice with tetrahydrofuran, 30 g for each time. Organic phases were combined and distilled to recover tetrahydrofuran. 40 g of methyl tert-butyl ether was charged to the residue, then mashed and washed, and filtered to obtain 45.7 g of N,N-di(p-methoxybenzyl)-5R-[(benzyloxy)amino] piperidine-2S-formamide in a yield of 93.5% and a purity of 99.93% in HPLC.

NMR (Nuclear Magnetic Resonance) data of the resulting product are provided below: $^1$HNMR (400 MHz, DMSO-d$_6$)

$^1$H-NMR (400 MHz, DMSO-d6) δ: 1.15 (1H, q), 1.34 (1H, q), 1.88 (2H, d), 2.30 (1H, t), 2.90 (1H, m), 3.01 (1H, d), 3.21 (1H, d), 3.80 (6H, s), 4.46 (4H, s), 4.76 (2H, s), 6.48 (1H, d), 6.90 (4H, d), 7.25 (4H, d), 7.55 (5H, m).

Example 4: Preparation of N,N-di(p-methylbenzyl)-5R-[(benzyloxy) amino] piperidine-2S-formamide (V$_3$)

To a 500 ml 4-neck flask equipped with a stirrer and a thermometer were charged 250 g of 2-methyltetrahydrofuran, 30.0 g of potassium carbonate, 39.5 g (0.1 mol) of tert-butyl 5R-[(benzyloxy)amino]piperidine-2S-carboxylate oxalate (III), and 40 g (0.18 mol) of di(p-methyl)benzylamine, and then the reaction mixture was stirred for 4 hours between 60° C. to 65° C., then cooled to 20° C.~25° C., and filtered. The filter cake was washed twice with 2-methyltetrahydrofuran, 30 g for each time. Organic phases were combined and distilled to recover 2-methyltetrahydrofuran. 40 g of methyl tert-butyl ether was charged to the residue, then mashed and washed, and filtered to obtain 43.6 g of N,N-di(p-methylbenzyl)-5R-[(benzyloxy) amino] piperidine-2S-formamide in a yield of 95.5% and a purity of 99.89% in HPLC.

NMR (Nuclear Magnetic Resonance) data of the resulting product are provided below: $^1$HNMR (400 MHz, DMSO-d$_6$)

$^1$H-NMR (400 MHz, DMSO-d6) δ: 1.13 (1H, q), 1.31 (1H, q), 1.85 (2H, d), 2.06 (6H, s), 2.27 (1H, t), 2.85 (1H, m), 2.91 (1H, d), 3.17 (1H, d), 4.60 (4H, s), 4.78 (2H, s), 6.54 (1H, d), 7.08 (4H, d), 7.19 (4H, d), 7.48 (5H, m).

Structural Formulae of Compounds V$_1$, V$_2$, and V$_3$ are as follows:

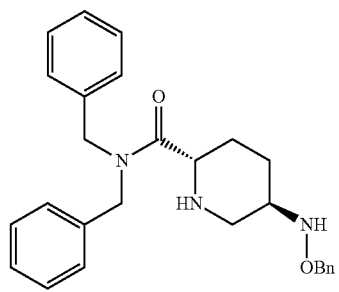

V$_1$

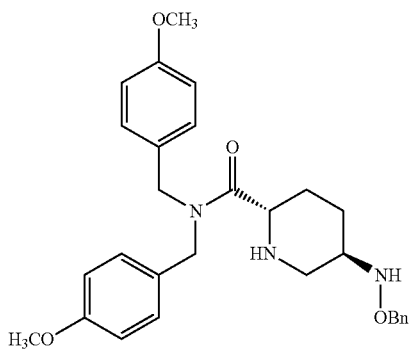

V$_2$

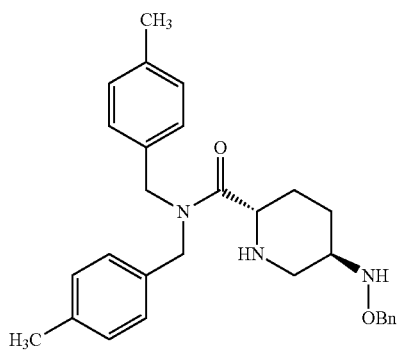

V$_3$

Example 5: Preparation of N,N-dibenzyl-(2S, 5R)-6-benzyloxy-7-oxo-1,6-diazabicyclo[3.2.1]oct-2-formamide (VI$_1$)

To a 1000 ml 4-neck flask equipped with a stirrer and a thermometer were charged 250 g of tetrahydrofuran, 43 g (0.1 mol) of N, N-dibenzyl-5R-[(benzyloxy)amino]piperidine-2S-formamide (V$_1$) prepared according to Example 1, and 50 g of triethylamine, and then cooled to −10° C.~0° C., then charged 30 g (0.1 mol) of triphosgene and 100 g of tetrahydrofuran solution, and then the reaction mixture was stirred for 8 hours between 10~20° C. The reaction liquid was poured into a 400 g of ice-water mixture and separated, and aqueous phase was extracted thrice with dichloromethane, 100 g for each time. Organic phases were combined, and then washed twice with saturated aqueous solution of sodium chloride, 50 g for each time; after the solvent was recovered from the resulting organic phase, 60 g of methyl tert-butyl ether was added to the residue; the residue was mashed, washed, and then filtered, to obtain 42.1 g of N,N-dibenzyl-(2S, 5R)-6-benzyloxy-7-oxo-1,6-diazabicyclo[3.2.1]oct-2-formamide in a yield of 92.5% and a purity of 99.96% in HPLC.

NMR (Nuclear Magnetic Resonance) data of the resulting product are provided below: $^1$H-NMR (400 MHz, DMSO-d6) δ: 1.65 (2H, m), 1.84 (1H, br), 2.06 (1H, m), 2.90 (2H, s), 3.62 (1H, s), 4.58 (4H, s), 4.93 (2H, dd), 7.28~7.47 (15H, m).

Example 6: Preparation of N,N-dibenzyl-(2S, 5R)-6-benzyloxy-7-oxo-1,6-diazabicyclo[3.2.1]oct-2-formamide (Vii)

To a 500 ml 4-neck flask equipped with a stirrer and a thermometer were charged 60 g of tetrahydrofuran, 4.3 g (0.01 mol) of N, N-dibenzyl-5R-[(benzyloxy)amino]piperidine-2S-formamide (V$_1$) prepared according to Example 1, and 5.0 g of tri-n-butylamine, and then cooled to −10° C.-0° C., then charged 3.0 g (0.015 mol) of diphosgene and 20 g of tetrahydrofuran solution, and then the reaction mixture was stirred for 8 hours between 10~20° C. The reaction liquid was poured into a 200 g of ice-water mixture and separated, and aqueous phase was extracted thrice with dichloromethane, 50 g for each time. Organic phases were combined, and then washed twice with saturated aqueous solution of sodium chloride, 20 g for each time; after the solvent was recovered from the resulting organic phase, 20 g of methyl tert-butyl ether was added to the residue; the residue was mashed, washed, and then filtered, to obtain 4.15 g of N,N-dibenzyl-(2S, 5R)-6-benzyloxy-7-oxo-1,6-diazabicyclo[3.2.1]oct-2-formamide in a yield of 91.2% and a purity of 99.9% in HPLC.

Example 7: Preparation of N,N-di (p-methoxy) benzyl-(2S,5R)-6-benzyloxy-7-oxo-1,6-diazabicyclo[3.2.1]oct-2-formamide (VI$_2$)

To a 500 ml 4-neck flask equipped with a stirrer and a thermometer were charged 100 g of dichloromethane, 4.9 g (0.01 mol) of N,N-di(p-methoxybenzyl)-5R-[(benzyloxy)amino]piperidine-2S-formamide (V$_2$) prepared according to Example 3, and 5.0 g of tri-n-butylamine, and then cooled to −10° C.~0° C., then charged 3.0 g (0.01 mol) of triphosgene and 20 g of dichloromethane solution, and then the reaction mixture was stirred for 8 hours between 10~20° C. The reaction liquid was poured into a 200 g of ice-water mixture and separated, and aqueous phase was extracted thrice with dichloromethane, 50 g for each time. Organic phases were combined, and then washed twice with saturated aqueous solution of sodium chloride, 20 g for each time; after the solvent was recovered from the resulting organic phase, 20 g of methyl tert-butyl ether was added to the residue; the residue was mashed, washed, and then filtered to obtain 4.75 g of N,N-di (p-methoxy) benzyl-(2S,5R)-6-benzyloxy-7-oxo-1,6-diazabicyclo[3.2.1]oct-2-formamide in a yield of 92.2% and a purity of 99.92% in HPLC.

NMR (Nuclear Magnetic Resonance) data of the resulting product are provided below: $^1$H-NMR (400 MHz, DMSO-d6) δ: 1.60 (2H, m), 1.81 (1H, br), 2.02 (1H, m), 2.88 (2H, s), 3.59 (1H, s), 3.62 (1H, d), 3.78 (6H, s), 4.55 (4H, s), 4.85 (2H, dd), 6.82 (4H, d), 7.16 (4H, d), 7.47 (5H, m).

Example 8: Preparation of N,N-di(p-methyl)benzyl-(2S,5R)-6-benzyloxy-7-oxo-1,6-diazabicyclo[3.2.1]oct-2-formamide (VI$_3$)

To a 500 ml 4-neck flask equipped with a stirrer and a thermometer were charged 100 g of dichloromethane, 4.6 g (0.01 mol) of N,N-di(p-methylbenzyl)-5R-[(benzyloxy)amino]piperidine-2S-formamide (V$_3$) prepared according to Example 4, and 4.0 g of triethylamine, and then cooled to 0° C.-10° C., then charged 3.0 g (0.01 mol) of triphosgene and 20 g of dichloromethane solution, and then the reaction mixture was stirred for 6 hours between 20~30° C. The reaction liquid was poured into a 200 g of ice-water mixture and separated, and aqueous phase was extracted thrice with dichloromethane, 50 g for each time. Organic phases were combined, and then washed twice with saturated aqueous solution of sodium chloride, 20 g for each time; after the solvent was recovered from the resulting organic phase, 20 g of methyl tert-butyl ether was added to the residue; the residue was mashed, washed, and then filtered to obtain 4.47 g of N,N-di(p-methyl)benzyl-(2S,5R)-6-benzyloxy-7-oxo-1,6-diazabicyclo[3.2.1]oct-2-formamide in a yield of 92.5% and a purity of 99.96% in HPLC.

NMR (Nuclear Magnetic Resonance) data of the resulting product are provided below: $^1$H-NMR (400 MHz, DMSO-d6) δ: 1.63 (2H, m), 1.85 (1H, br), 2.05 (1H, m), 2.10 (6H, s), 2.91 (2H, s), 3.62 (1H, s), 3.68 (1H, d), 3.83 (6H, s), 4.61 (4H, s), 4.88 (2H, dd), 6.84 (4H, d), 7.19 (4H, d), and 7.51 (5H, m).

Structural Formulae of Compounds VI$_1$, VI$_2$, and VI$_3$ are as follows:

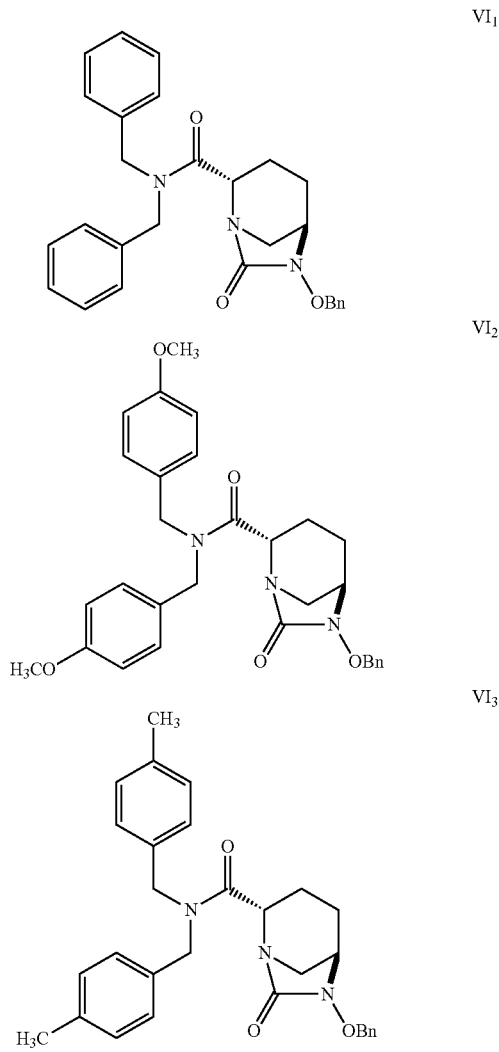

Example 9: Preparation of ({[(2S,5R)-2-carbamoyl-7-oxo-1,6-diazabicyclo[3.2.1]oct-6-yl]oxy}sulfonyl) tetrabutylammonium salt To a stainless steel reactor were charged 14 g of isopropanol, 17 g of water, 4.9 g (0.01 mol) of N,N-dibenzyl-(2S,5R)-6-benzyloxy-7-oxo-1,6-diazabicyclo[3.2.1]oct-2-formamide (VI$_1$) prepared according to the process of Example 5, 1.56 g (0.0112 mol) of sulfur trioxide-trimethylamine, 0.2 g (0.002 mol) of triethylamine, and 0.11 g of palladium-on-carbon (with a water content of 55 wt %) with a palladium mass content of 10%; after the caldron was closed, nitrogen gas protection was introduced. The reactor was intermittently introduced with hydrogen to maintain the pressure of hydrogen gas at 0.07~0.13 Mpa; the reactor was insulated at the room temperature for 1 hour, till the raw material VI$_1$ was completely reacted (at this point, the pressure would rise). After replacement with the nitrogen gas, the reactor continued to be insulated at the room temperature for another 1.5 h. After 0.16 g (0.0026 mol) of acetic acid was charged to neutralize, the palladium-on-carbon was filtered out, and the filter cake was washed with 8.6 g of water. The filtrate was washed with 26 ml of n-butyl acetate and separated, and then the aqueous phase was taken.

3.68 g (0.0122 mol) of tetrabutylammonium acetate and 0.06 g (0.001 mol) of acetic acid were pre-dissolved into 6.5 g of water to prepare a tetrabutylammonium acetate solution. 70 wt % of tetrabutylammonium acetate solution was charged into the washed and separated aqueous phase and salinized at the room temperature for 1~2 h. 26 ml of dichloromethane was applied to extract organic phases; the solution was then separated to obtain organic phases. The remaining 30 wt % of tetrabutyl ammonium acetate solution was charged into the organic phase and salinized at the room temperature for 1~2 h, and then extracted with 9 ml of dichloromethane. After the organic phases were combined and concentrated to 20 ml. Then, 50 ml methyl isobutyl ketone was charged, and then the mixture was concentrated to 40 ml and cooled to 0° C., and filtered. The filter cake was then washed with 10 ml of methyl isobutyl ketone, and then vacuum dried, and finally 4.5 g of ({[(2S,5R)-2-carbamoyl-7-oxo-1,6-diazabicyclo[3.2.1]oct-6-yl]oxy}sulfonyl)tetrabutylammonium salt (II) was obtained in a yield of 88.7% and a purity of 99.3% in HPLC.

NMR (Nuclear Magnetic Resonance) data of the resulting product are provided below: $^1$H-NMR (400 MHz, CDCl$_3$) δ: 1.00 (12H, t), 1.45 (8H, m), 1.67 (9H, m), 1.87 (1H, m), 2.16 (1H, m), 2.37 (1H, dd), 2.87 (1H, d), 3.31 (9H, m), 3.91 (1H, d), 4.33 (1H, s), 5.87 (1H, s), 6.69 (1H, s).

Example 10: Preparation of ({[(2S,5R)-2-carbamoyl-7-oxo-1,6-diazabicyclo [3.2.1] oct-6-yl]oxy}sulfonyl)tetrabutylammonium salt (II)

To a hydrogenation reaction caldron were charged 16 g of isopropanol, 20 g of water, 4.9 g (0.01 mol) of N,N-di (p-methoxy) benzyl-(2S,5R)-6-benzyloxy-7-oxo-1,6-diazabicyclo[3.2.1]oct-2-formamide (VI$_2$) prepared according to Example 7, 1.56 g (0.0112 mol) of sulfur trioxide-trimethylamine, 0.2 g (0.002 mol) of triethylamine, and 0.12 g of palladium-on-carbon (with a water content of 55 wt %) with a palladium mass content of 10%; after the reactor was closed, nitrogen gas protection was applied. The reactor was intermittently introduced with hydrogen to maintain the pressure of hydrogen gas at 0.07~0.13 MPa; the reactor was insulated at the room temperature for 1 hour, till the raw material VI$_2$ was completely reacted (at this point, the pressure would rise). After replacement with the nitrogen gas, the reactor continued to be insulated at the room temperature for another 1.5 h. After 0.16 g (0.0026 mol) of acetic acid was charged to neutralize, the palladium-on-carbon was filtered out, and the filter cake was washed with 10 g of water. The filtrate was washed with 30 ml of n-butyl acetate and separated, and then the aqueous phase was taken.

3.68 g (0.0122 mol) of tetrabutylammonium acetate and 0.06 g (0.001 mol) of acetic acid were pre-dissolved into 7.5 g of water to prepare a tetrabutylammonium acetate solution. 70 wt % of tetrabutyl ammonium acetate solution was charged into the washed and separated aqueous phase and salinized at the room temperature for 1~2 h. 30 ml of dichloromethane was applied to extract organic phases; the solution was then separated to obtain organic phases. The remaining 30 wt % of tetrabutylammonium acetate solution was charged into the organic phase and salinized at the room temperature for 1~2 h, and then the mixture was extracted with 10 ml of dichloromethane, the organic phases were combined and concentrated to 20 ml. Then, 50 ml of methyl isobutyl ketone was charged, and then the mixture was concentrated to 40 ml and cooled to 0° C., and filtrated. The filter cake was then washed with 10 ml of methyl isobutyl ketone, and then vacuum dried, and finally 4.7 g of ({[(2S,5R)-2-carbamoyl-7-oxo-1,6-diazabicyclo[3.2.1]oct-6-yl]oxy}sulfonyl)tetrabutylammonium salt (II) was obtained in a yield of 92.7% and a purity of 99.1% in HPLC.

Example 11: Preparation of ({[(2S,5R)-2-carbamoyl-7-oxo-1,6-diazabicyclo [3.2.1] oct-6-yl]oxy}sulfonyl)tetrabutylammonium salt (II)

To a hydrogenation reaction caldron were charged 15 g of isopropanol, 18 g of water, 4.6 g (0.01 mol) of N,N-di (p-methyl) benzyl-(2S,5R)-6-benzyloxy-7-oxo-1,6-diazabicyclo[3.2.1]oct-2-formamide (VI$_3$) prepared according to Example 8, 1.56 g (0.0112 mol) of sulfur trioxide-trimethylamine, 0.2 g (0.002 mol) of triethylamine, and 0.11 g of palladium-on-carbon (with a water content of 55 wt %) with a palladium mass content of 10%; after the reactor was closed, nitrogen gas protection was applied. The reactor was intermittently introduced with hydrogen to maintain the pressure of hydrogen gas at 0.07~0.13 MPa; the reactor was insulated at the room temperature for 1 hour, till the raw material VI$_3$ was completely reacted (at this point, the pressure would rise). After replacement with the nitrogen gas, the reactor continued to be insulated for 1.5 h at the room temperature. After 0.16 g (0.0026 mol) of acetic acid was charged to neutralize, the palladium-on-carbon was filtered out, and the filter cake was washed with 8.6 g of water. The filtrate was washed with 26 ml of n-butyl acetate and separated, and then the aqueous phase was taken.

3.68 g (0.0122 mol) of tetrabutylammonium acetate and 0.06 g (0.001 mol) of acetic acid were pre-dissolved into 6.5 g of water to prepare a tetrabutylammonium acetate solution. 70 wt % of tetrabutylammonium acetate solution was charged into the washed and separated aqueous phase and salinized at the room temperature for 1~2 h. 26 ml of dichloromethane was applied to extract organic phases; the solution was then separated to obtain organic phases. The remaining 30 wt % of tetrabutyl ammonium acetate solution was charged into the organic phase and salinized at the room temperature for 1~2 h, and then the mixture was extracted with 9 ml of dichloromethane, the organic phases were combined and concentrated to 20 ml. Then, 50 ml of methyl isobutyl ketone was charged, and then the mixture was concentrated to 40 ml, cooled to 0° C., and filtrated. Then, the filter cake was washed with 10 ml of methyl isobutyl ketone, and then vacuum dried, finally 4.4 g of ({[(2S,5R)-2-carbamoyl-7-oxo-1,6-diazabicyclo[3.2.1]oct-6-yl]oxy}sulfonyl)tetrabutylammonium salt (II) was obtained in a yield of 86.8% and a purity of 99.4% in HPLC.

The invention claimed is:

1. A process for preparing the chemical compound of formula II, comprising the following steps:
   (1) the compound of Formula III is reacted with an amide of Formula IV in solvent A and in the presence of base A via an amidation reaction to obtain a compound of Formula V;

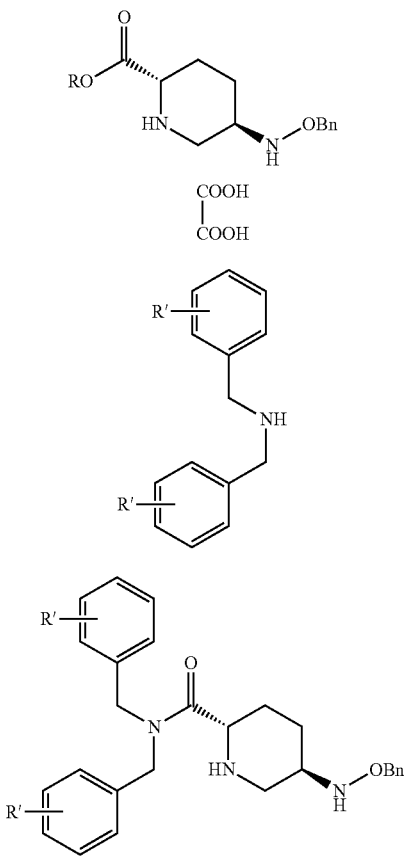

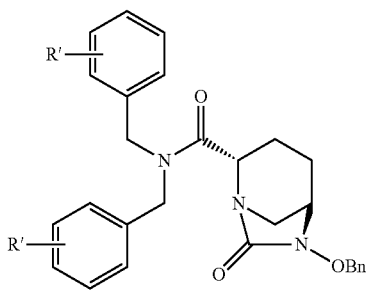

wherein in the compound of Formula III: R is a $C_{1-6}$ aliphatic group or alkyl-substituted phenyl;

in the compound of Formula IV: R' is selected from the group consisting of hydrogen, o-methoxy, o-methyl, p-methoxy and p-methyl;

R' in the compound of formula V is identical to R' in the compound of formula IV;

(2) the compound of formula V is reacted with a carbonylation reagent in solvent B and in the presence of base B via urea cyclization to obtain the compound of Formula VI;

wherein R' in the compound of formula VI is identical to R' in the compound of formula IV;

(3) in solvent C and in the presence of base C, the benzyl or the substituted benzyl in the compound of Formula VI is removed by catalytic hydrogenation, then the resulting compound is sulfatated by sulfur trioxide complex, to obtain a product; then, the product is salinized into tetrabutylammonium to obtain the compound of Formula II

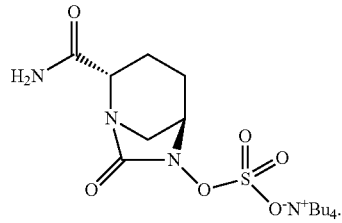

2. The process according to claim 1, wherein the solvent A in step (1) is selected from the group consisting of dichloromethane, 1,2-dichloroethane, trichloromethane, tetrachloromethane, tetrahydrofuran, 2-methyltetrahydrofuran, methoxycyclopentane, methylbenzene, and combinations of two or more thereof; and in step (1), a mass ratio between the solvent A and the compound of Formula III is 4~20:1; and the base A is an inorganic base or an organic base; the inorganic base is one of potassium carbonate or sodium carbonate, or a mixture of the two, and the organic base is dibenzylamine; and a molar ratio between the base A and the compound of Formula III is 2.0~5.0:1.

3. The process according to claim 1, wherein in step (1), the amide of Formula IV is selected from the group consisting of dibenzylamine, di(o-methoxy) benzylamine, di(p-methoxy) benzylamine, di(o-methyl) benzylamine, and di(p-methyl) benzylamine;

a molar ratio between the amide of Formula IV and the compound of Formula III is 1~4:1.

4. The process according to claim 1, wherein in step (1), the amidation reaction is conducted in the temperature of from 0° C. to 100° C.

5. The process according to claim 1, wherein in step (2), the solvent B is selected from the group consisting of dichloromethane, 1,2-dichloroethane, trichloromethane, tetrachloromethane, tetrahydrofuran, 2-methyltetrahydrofuran, methoxycyclopentane, n-butanol, tert-butanol or methylbenzene, and combinations of two or more thereof; and in step (2), a mass ratio between the solvent B and the compound of formula V is 4~27:1.

6. The process according to claim 1, wherein in step (2), a molar ratio between the carbonylation reagent and the compound of formula V is 0.3~3:1.

7. The process according to claim 1, wherein in step (2), the carbonylation reagent is selected from the group consisting of triphosgene, diphosgene, carbonyldiimidazole and di-tert-butyl dicarbonate;

a molar ratio between triphosgene and the compound of formula V is 0.3~1.5:1; a molar ratio between diphosgene and the compound of formula V is 0.5~2.0:1; and a molar ratio between carbonyldiimidazole or di-tert-butyl dicarbonate and the compound of formula V is 1.0~3.0:1.

8. The process according to claim 1, wherein in step (2), the temperature for the urea cyclization reaction ranges from −20° C. to 100° C.

9. The process according to claim 1, wherein in step (3), the solvent C is selected from the group consisting of isopropanol, n-butanol, tert-butanol, tetrahydrofuran, N,N-dimethyl formamide, water, and mixtures of two or more thereof; and in step (3), a mass ratio between the solvent C and the compound of Formula VI is 4~20:1.

10. The process according to claim 1, wherein in step (3), the reaction temperatures for the catalytic hydrogenolysis and the sulfatation both range from −10° C. to 60° C.

11. The process according to claim 4, wherein in step (1), the amidation reaction is conducted in the temperature of from 30° C. to 80° C.

12. The process according to claim 5, wherein in step (2), the base B is an organic base; and the molar ratio between the base B and the compound of formula V is 2~6:1.

13. The process according to claim 8, wherein in step (2), the temperature for the urea cyclization reaction ranges from 10 to 40° C.

14. The process according to claim 9, wherein in step (3), the base C is organic base; and a molar ratio between the base C and the compound of Formula VI is 0.1-0.3:1;
the catalyst for the catalytic hydrogenolysis is palladium-on-carbon with 5% mass content 15 of palladium or palladium-on-carbon with 10% mass content of palladium; in the palladium-on-carbon, the water content is 5~55 wt %; in step (3), the mass of the catalyst for the catalytic hydrogenolysis is 1.0~20.0% of the mass of the compound of formula VI; and the hydrogen pressure used for the catalytic hydrogenolysis is 0.05~0.30 Mpa;
the sulfur trioxide complex is one of trimethylamine sulfur trioxide, pyridine sulfur 20 trioxide, or triethylamine sulfur trioxide;
the tetrabutyl ammonium source used for the tetrabutylammonium salinization is tetrabutylammonium hydroxide or tetrabutylammonium acetate; and a molar ratio between the tetrabutyl ammonium source used for the tetrabutylammonium salinization and the compound of formula VI is 0.8~1.2:1.

15. The process according to claim 10, wherein in step (3), the reaction temperature for the tetrabutylammonium salinization ranges from 0° C. to 50° C.

16. The process according to claim 15, wherein in step (3), the reaction temperature for the tetrabutylammonium salinization ranges from 10° C. to 30° C.

17. The process according to claim 1, wherein in the compound of Formula III: R is selected from the group consisting of methyl, ethyl, n-propyl, isopropyl, n-butyl, isobutyl, tert-butyl, n-pentyl, isopentyl, tert-amyl, hexyl, benzyl, o-methylbenzyl and p-methylbenzyl.

18. The process according to claim 10, wherein the reaction temperatures for the catalytic hydrogenolysis and the sulfatation both range from 10° C. to 40° C.

19. The process according to claim 14, wherein the molar ratio between the sulfur trioxide complex and the compound of formula VI is 1.0~2.0:1.

* * * * *